(12) United States Patent
Kaal et al.

(10) Patent No.: US 8,114,050 B2
(45) Date of Patent: *Feb. 14, 2012

(54) CONTROLLED RETRACTION SYRINGE AND PLUNGER THEREFOR

(75) Inventors: Joseph Hermes Kaal, Morpeth (AU); Craig Stephen Thorley, Largs (AU); Damien Judd, Coomera Springs (AU)

(73) Assignee: Unitract Syringe Pty Ltd, Sydney, New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 11/914,092

(22) PCT Filed: May 11, 2006

(86) PCT No.: PCT/AU2006/000618
§ 371 (c)(1),
(2), (4) Date: May 15, 2008

(87) PCT Pub. No.: WO2006/119570
PCT Pub. Date: Nov. 16, 2006

(65) Prior Publication Data
US 2009/0221962 A1 Sep. 3, 2009

Related U.S. Application Data

(60) Provisional application No. 60/732,777, filed on Nov. 2, 2005.

(30) Foreign Application Priority Data

May 12, 2005 (AU) .................................. 2005902392
Aug. 8, 2005 (AU) .................................. 2005904256

(51) Int. Cl.
*A61M 5/00* (2006.01)

(52) U.S. Cl. ........................................................ 604/110
(58) Field of Classification Search .................. 604/195, 604/110, 196, 187, 220
See application file for complete search history.

(56) References Cited

U.S. PATENT DOCUMENTS 5,098,402 A * 3/1992 Davis ............................ 604/195
5,114,404 A * 5/1992 Paxton et al. ................. 604/110
(Continued)

FOREIGN PATENT DOCUMENTS
WO 9404207 A1 3/1994
(Continued)

*Primary Examiner* — Matthew F DeSanto
(74) *Attorney, Agent, or Firm* — LeClairRyan, a Professional Corporation

(57) ABSTRACT

A retractable syringe (10) and plunger (20) therefore are provided, the syringe having a barrel (20), a retractable needle mount (40) to which is mounted or is mountable a needle (11), and a plunger (80), the plunger comprising an initially compressed spring (60), a means for engaging the retractable needle mount, an integrally formed plunger seal (22) and a removable controlling means (70) for facilitating control of the rate of retraction of needle mount when engaged with plunger. The needle mount is held in the barrel by a holding means which prevents inadvertent retraction of the needle mount when the plunger is withdrawn to fill the syringe. The holding means comprises a plurality of clips (196A, 196B, 196C) that may be integrally formed with the barrel or may be present on a cap mounted to the barrel. An ejector means (52) is also provided, whereby plunger depression can urge the ejector means to release the needle from the holding means and thereby allow retraction of the needle mount following decompression of the spring.

20 Claims, 17 Drawing Sheets

U.S. PATENT DOCUMENTS

| | | | |
|---|---|---|---|
| 5,211,628 A * | 5/1993 | Marshall | 604/110 |
| 5,215,533 A * | 6/1993 | Robb | 604/195 |
| 5,531,694 A * | 7/1996 | Clemens et al. | 604/110 |
| 5,681,292 A * | 10/1997 | Tober et al. | 604/195 |
| 5,702,367 A | 12/1997 | Cover et al. | |
| 6,050,977 A * | 4/2000 | Adams | 604/195 |
| 6,090,078 A | 7/2000 | Erskine | |
| 6,706,019 B1 * | 3/2004 | Parker et al. | 604/198 |
| 2004/0215150 A1 * | 10/2004 | Shue et al. | 604/192 |
| 2005/0177100 A1 | 8/2005 | Harper et al. | |
| 2006/0069348 A1 * | 3/2006 | Parker et al. | 604/110 |
| 2006/0129096 A1 * | 6/2006 | Wright | 604/110 |

FOREIGN PATENT DOCUMENTS

| | | |
|---|---|---|
| WO | 0018466 A1 | 4/2000 |
| WO | 0151107 A1 | 7/2001 |

* cited by examiner

CONTROLLED RETRACTION SYRINGE AND PLUNGER THEREFOR

This application is a national stage application under 35 U.S.C. §371 from PCT Application No. PCT/AU2006/000618, filed May 11, 2006, which claims the priority benefit of Australian Application Nos. 2005902392, filed May 12, 2005 and 2005904256, filed Aug. 8, 2005 and U.S. Provisional Application No. 60/732,777, filed Nov. 2, 2005.

FIELD OF THE INVENTION

THIS INVENTION relates to syringes. More particularly, this invention relates to a retractable syringe that includes a controllable retraction mechanism to prevent re-use of the syringe.

BACKGROUND OF THE INVENTION

The practice of sharing syringes without adequate sterilization between successive users is a major contributor to the transfer of Human Immunodeficiency Virus (HIV) and Hepatitis with subsequent severe repercussions for the sufferer and at a high cost to society for supporting and providing medical attention to sufferers.

In response to this problem, syringes have been developed with the aim of preventing syringe re-use.

One solution has been to develop syringes where the needle is permanently retractable into the barrel of the syringe, retraction driven by a compressed spring, as for example described in International Publication WO 01/80930. An improved "feel" may be provided for a syringe user such as by incorporating a pre-compressed spring that does not provide resistance to plunger depression, as described in International Publication WO 2004/082747.

However, spring decompression is relatively uncontrolled, which in use can lead to excessively forceful needle retraction that can result in blood splattering as air is forced from the syringe barrel as the needle retracts into the barrel.

Another problem associated with retractable syringes is that the plunger must be alignable with the retractable needle so that complementary engaging means located on the plunger and retractable needle do not engage prior to retraction, but can engage when required to facilitate needle retraction.

This requirement for correct orientation can add to the manufacture cost and sale price of the retractable syringe, which can detract from the commercial attractiveness of the retractable syringe, particularly in relation to mass production and mass distribution in third world countries.

SUMMARY OF THE INVENTION

The present invention is directed in one broad form to a retractable syringe which comprises a mechanism to facilitate needle retraction in a controlled manner.

The present invention is directed in another broad form to a retractable syringe having a means to prevent inadvertent retraction of the needle.

The present invention is directed in yet another broad form to a retractable syringe which does not require alignment between a retractable needle and a plunger, either during assembly or during use, to facilitate needle retraction.

In a first aspect, the invention provides a plunger for a retractable syringe having a barrel and a retractable needle mount to which is mounted or is mountable a needle, said plunger comprising a means for engaging said retractable needle mount and a removable controlling means for facilitating control of the rate of retraction of said retractable needle mount when engaged with said plunger.

In a second aspect, the retractable syringe having a barrel; a retractable needle mount to which is mounted or is mountable a needle; and a plunger comprising a means for engaging said retractable needle mount and a removable controlling means for facilitating control of the rate of retraction of said retractable needle mount when engaged with said plunger.

In a third aspect, the invention provides a method of operating a retractable syringe having a barrel; a retractable needle mount to which is mounted or is mountable a needle; and a plunger comprising a means for engaging said retractable needle mount and a removable controlling means, said method including the step of operating said removable controlling means to control the rate of retraction of said retractable needle mount when engaged with said plunger.

In a fourth aspect, the invention provides a method of manufacturing a plunger or syringe according to the aforementioned aspects, wherein said plunger is inserted into said syringe without aligning said plunger and a retractable needle mount to be engaged thereby.

Suitably, the plunger comprises a plunger seal, a plunger housing and a plunger member.

Preferably, said plunger seal is integrally formed or otherwise contiguous with said plunger housing, such as by insert moulding onto said plunger housing.

Typically, the integrally formed plunger seal is particularly suitable for use with a "fill-able" syringe (rather than a pre-filled syringe), as this provides a more simple and cost-effective means for manufacturing and assembling said retractable syringe while retaining sufficient sealing function.

Preferably, the plunger further comprising a biasing means, in use said plunger housing and said plunger member co-operating to releasably maintain said biasing means in an initially compressed state.

Said biasing means is a spring, elastic or other compressible and de-compressible structure.

Preferably, said biasing means is a spring.

In a preferred form, the retractable syringe further comprises a holding means that releasably engages said needle mount to thereby prevent retraction of the retractable needle mount during withdrawal of the plunger.

In one embodiment, the holding means comprises holding clips integrally formed in said barrel.

In another embodiment, the holding means comprises holding clips in a cap mounted to said barrel.

Suitably, the syringe further comprises an ejector means operable to release said holding means from engagement with said needle mount to thereby allow retraction of said needle mount.

In a preferred embodiment, in use uncoupling of said plunger housing and said plunger members facilitates decompression of said spring after said plunger member has engaged said needle mount, so that decompression of said spring retracts said plunger member and said needle mount when engaged therewith.

Suitably, the plunger further comprises a retaining means for releasably coupling said controlling means to said plunger housing prior to retraction of said retractable needle mount.

Preferably, the method of use includes the step of removing the controlling member from the plunger after retraction is complete.

In a preferred from, said controlling means is a control rod.

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE DRAWINGS

Non-limiting embodiments of the invention are described herein with reference to drawings wherein.

DETAILED DESCRIPTION OF THE INVENTION

Figure 1:
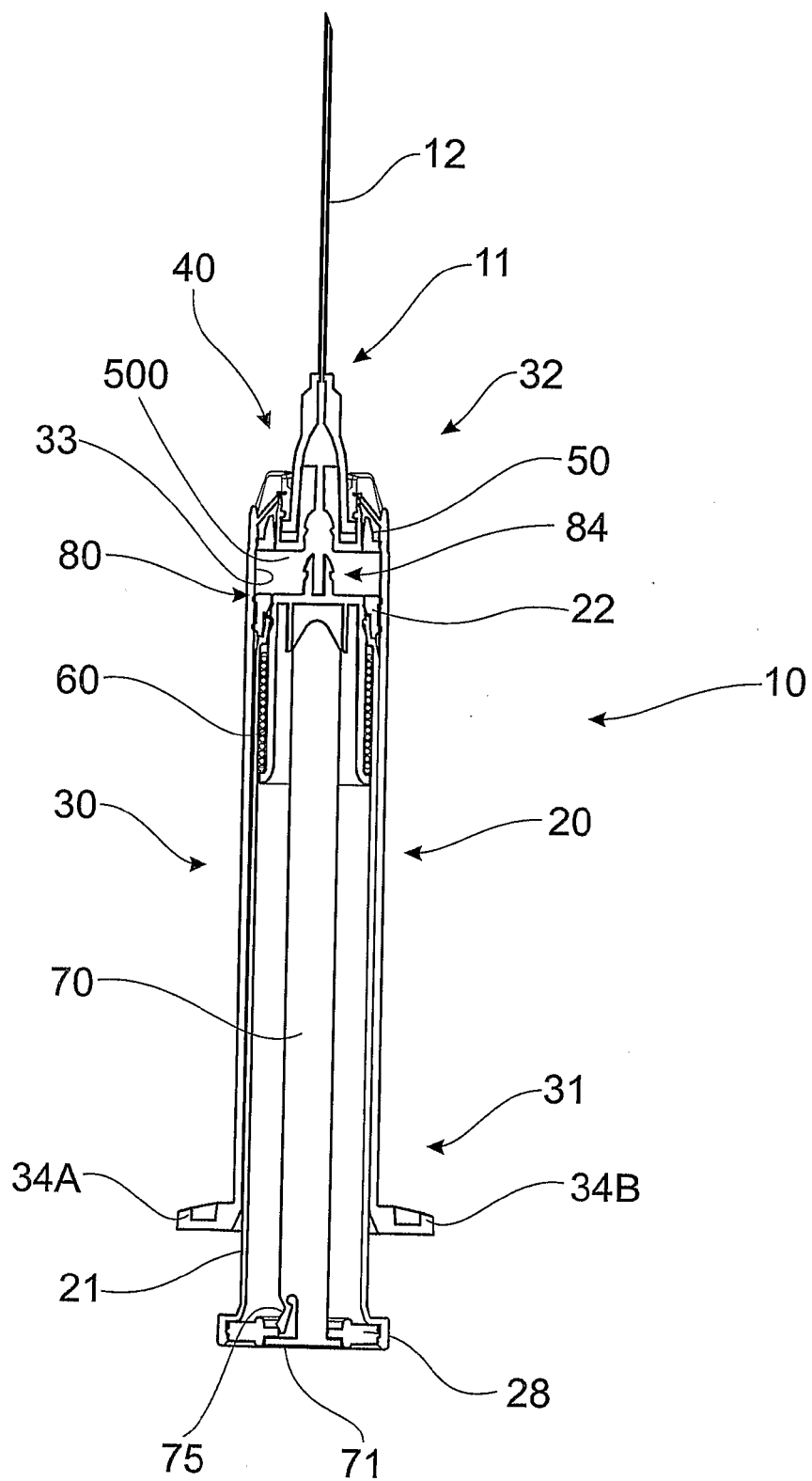
FIG. 1 is a sectional view of an embodiment of a retractable syringe.

Referring to FIG. 1, retractable syringe 10 comprises plunger 20 and barrel 30. Barrel 30 comprises plunger end 31, needle end 32, inside wall 33 and finger grips 34A, 34B at plunger end 31. At needle end 32 of barrel 30 is mounted retractable needle mount 40 with needle 11 comprising cannula 12 mounted thereto, and sealing member 50 fitted into circumferential notch 39 in inside wall 33.

Figure 3:
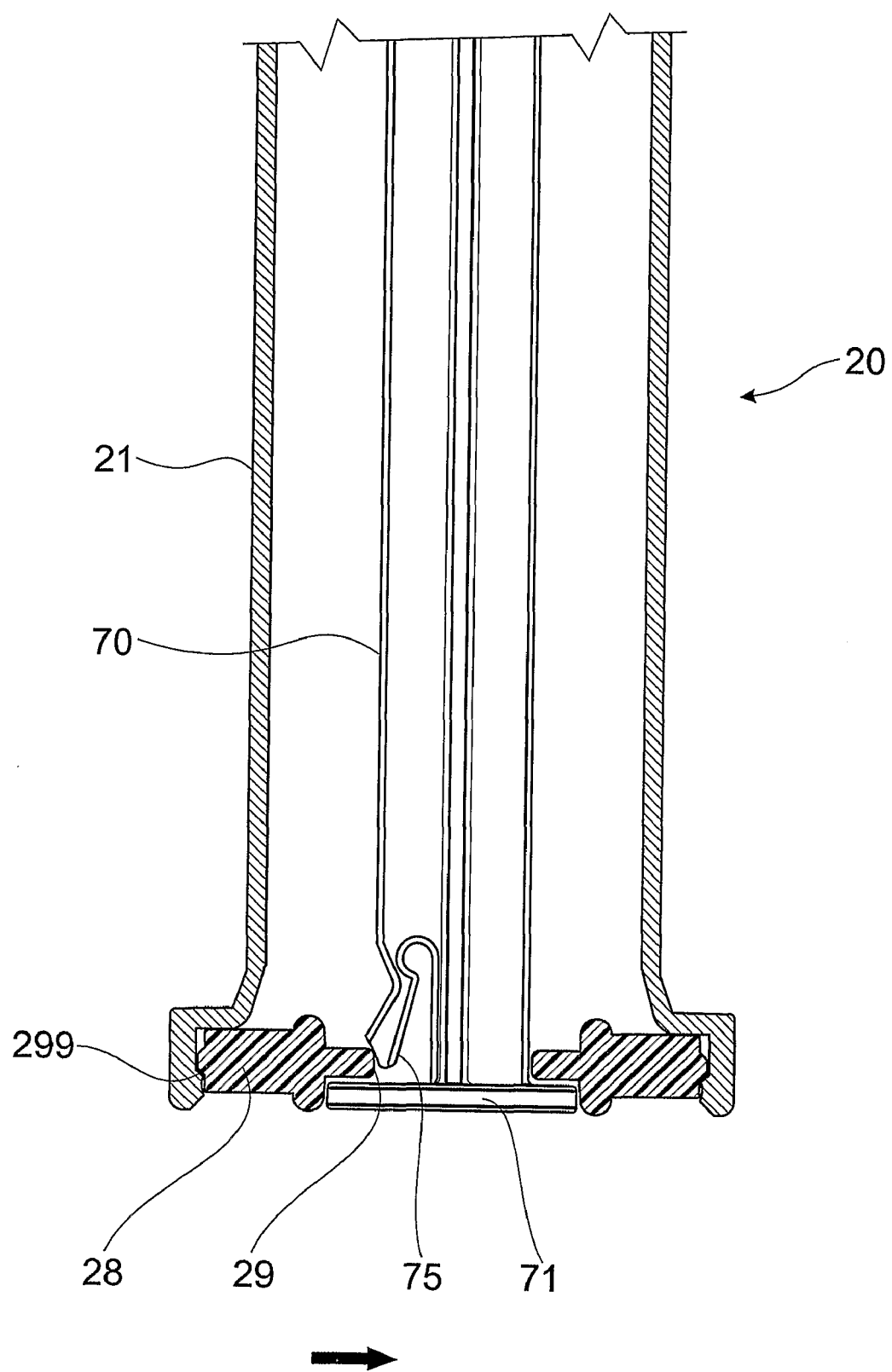
FIG. 3 is a side sectional view of an embodiment of a plunger showing a plunger rod engaged with a plug member in a plunger housing before retraction of the plunger rod.

Plunger 20 is axially moveable within fluid space 500 of barrel 30 comprises plunger housing 21 having plunger seal 22, control rod 70 and plunger member 80. Control rod 70 has button 71 which is operable by a user, fitted into annular plug member 28 fitted into internal flange 299 of plunger housing 21, as best shown in FIG. 3.

Figure 2:
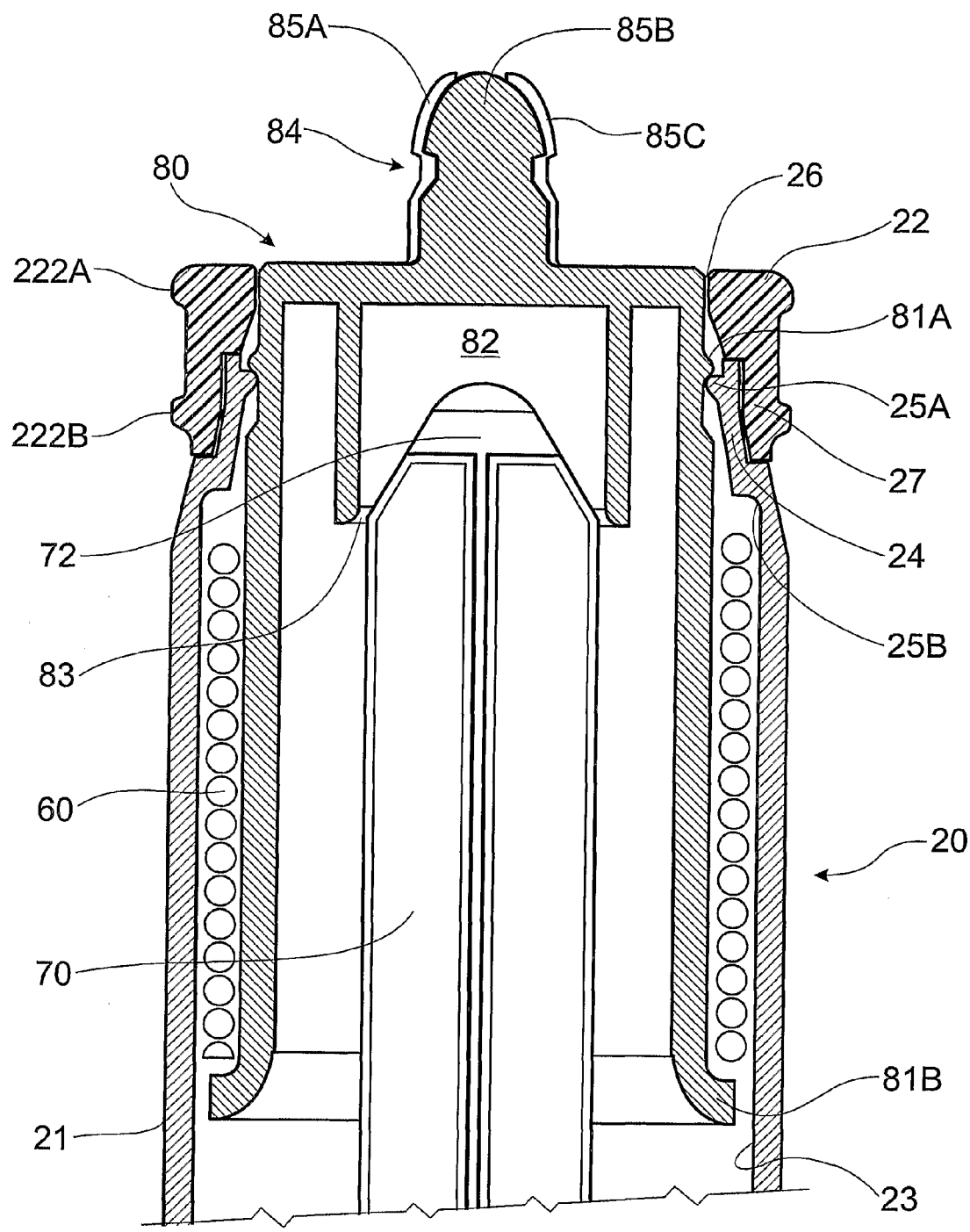
FIG. 2 is a side sectional view of an embodiment of a plunger showing a compressed spring maintained between a plunger member and plunger housing before retraction.

As evident in FIG. 2, plunger housing 21 is substantially hollow and comprises inner wall 23 and neck 24 with inner circumferential shoulders 25A, 25B. Plunger member 80 comprises outer circumferential ledges 81A, 81B and internal chamber 82 having ring 83 which receives and releasably engages complementary nub 72 of control rod 70.

Plunger seal 22 is integrally formed or otherwise contiguous with plunger housing 21, preferably by insert moulding into plunger housing 21, so that seat 27 of plunger seal 22 seals onto neck 24 of plunger housing 21 and bears against plunger member 80 at junction 26, whilst also providing a fluid seal between plunger sealing members 222A, 222B and inside wall 33 of barrel 30.

Compressed spring 60 is mounted to plunger member 80, held between outer circumferential ledge 81B of plunger member 80 and inner circumferential shoulder 25B of inner wall 23 of plunger housing 21. Outer circumferential ledge 81A of plunger member 80 bears against inner circumferential shoulder 25A of plunger housing 21 to thereby maintain releasable engagement between plunger housing 21 and plunger member 80.

As shown in FIG. 3, button 71 of plunger rod 70 is initially engaged with annular plug member 28 by way of spring clip 75 bearing against inner circumferential shoulder 29 of annular plug member 28. Annular plug member 28 is fitted into inner flange 299 of plunger housing 21, which thereby prevents inadvertent disengagement and retraction of plunger rod 70 from plunger housing 21 and, consequently, plunger member 80 until spring-driven retraction of plunger rod 70 is required.

Figure 4:
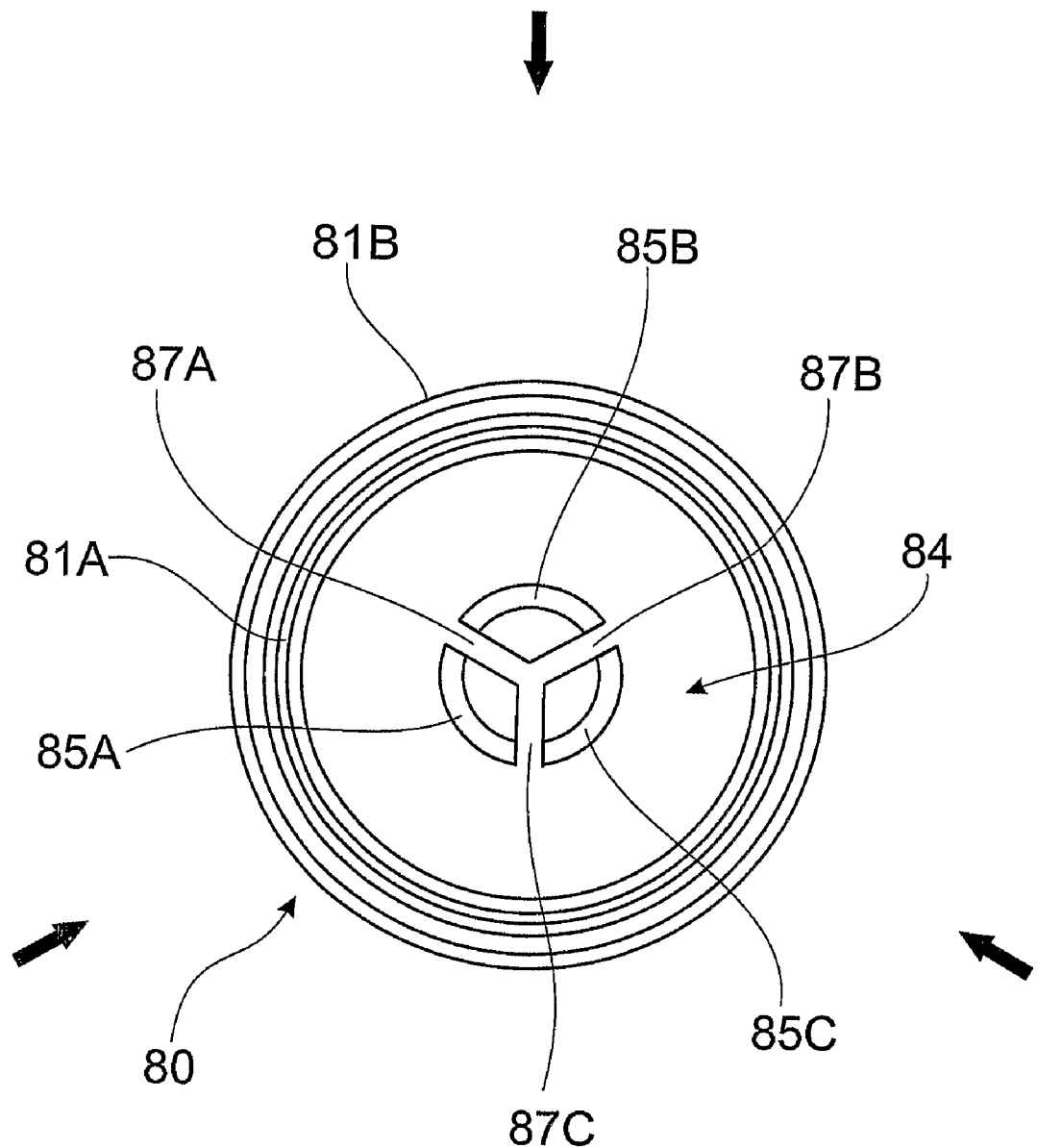
FIG. 4 is a top view of an embodiment of a plunger member showing a needle mount engaging means.

Referring to FIG. 4, plunger member 80 further comprises needle mount-engaging means 84 which comprises plurality of male members 85A, 85B, 85C separated by gaps 87A, 87B, 87C. Male members 85A, 85B, 85C are formed of a resilient material so as to be capable of radial inward movement as indicated by the solid arrows.

Figure 5:
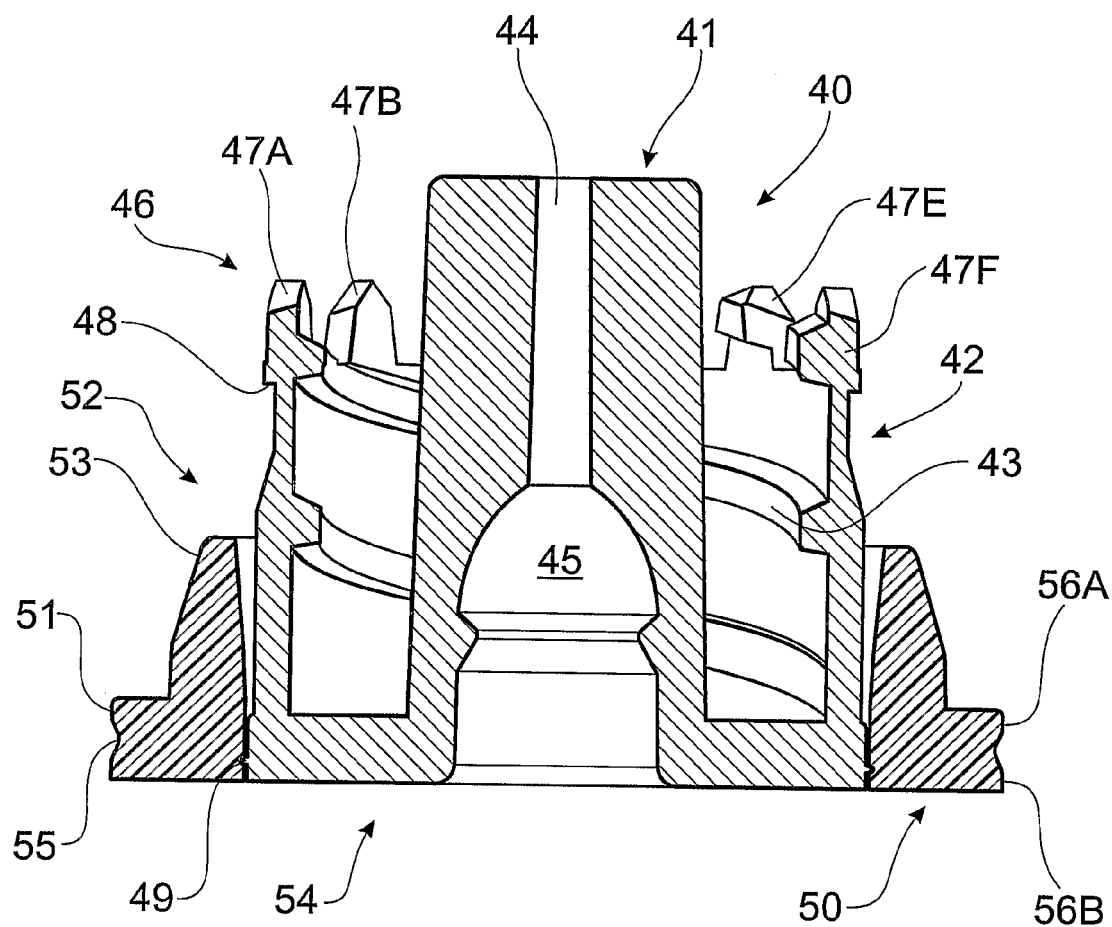
FIG. 5 is a side sectional view of an embodiment of a needle mount, sealing member and ejector means.

Referring to FIG. 5, needle mount 40 comprises body 42 having luer mount 41 with locking thread 43 and central bore 44 which allows fluid communication between needle 11 (not shown in FIG. 5) mounted to luer mount 41 and fluid contents of barrel 30.

In an alternative embodiment, luer mount 41 may be in the form of a non-threaded luer slip (not shown) as is well known in the art.

In another alternative embodiment, the invention contemplates retraction of a fixed needle 11 rather than removably mountable needle 11, as will be described in more detail hereinafter.

Central bore 44 of needle mount 40 communicates with mating recess 45 that receives needle mount-engaging means 84 of plunger 20 to facilitate retraction of needle mount 40 and a needle engaged therewith.

Needle mount body 42 further comprises serrated rim 46, which comprises plurality of teeth 47A-L and needle mount base 49.

Sealing member 50 comprises sealing base 51 that comprises sealing ribs 56A, 56B separated by waist 55, ejector means 52 in the form of tapered annulus 53 and needle mount passage 54.

Sealing member 50 is fitted around needle mount base 49.

Figure 6:
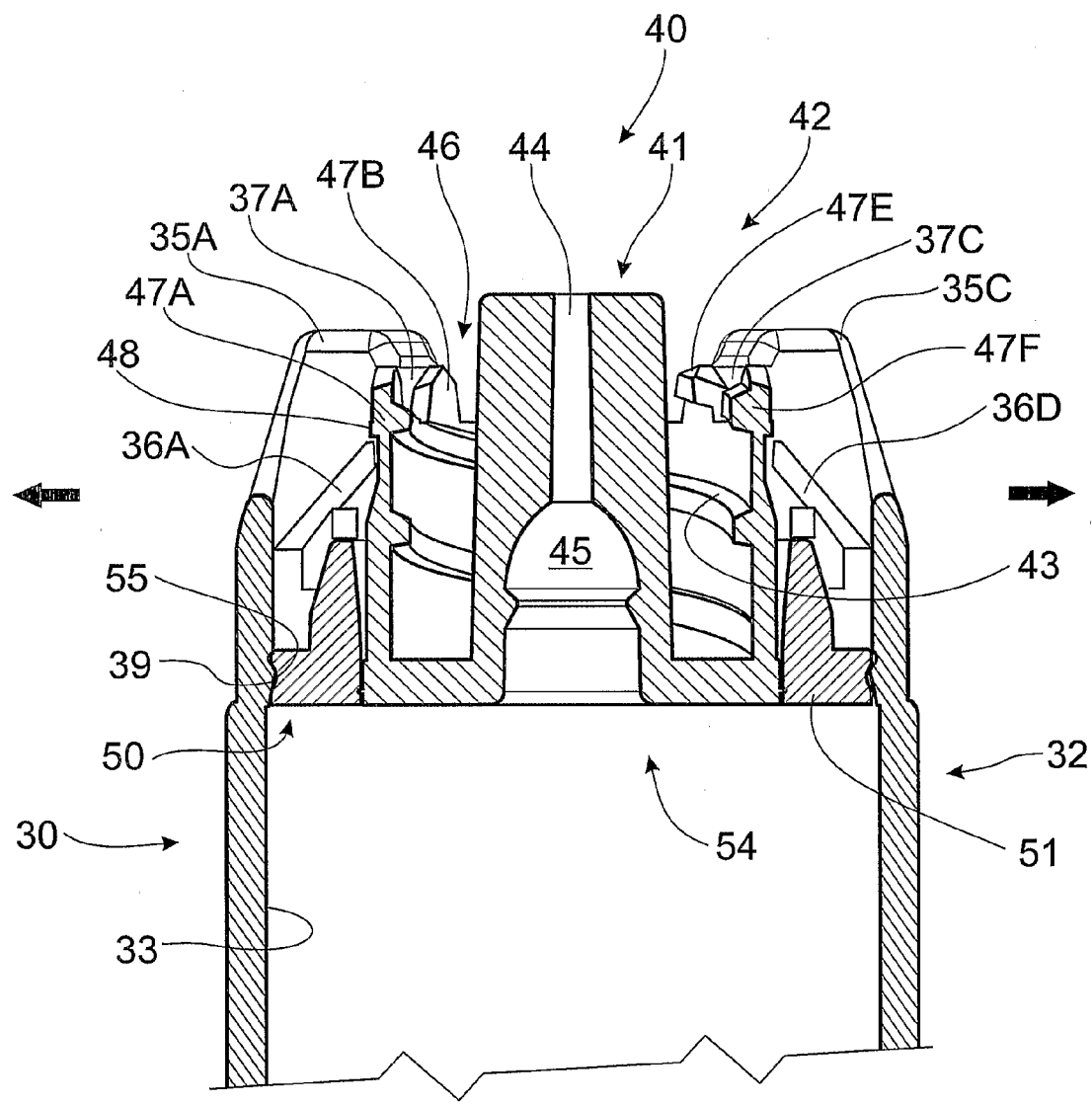
FIG. 6 is a sectional view of a barrel showing a needle mount engaged therewith before retraction.

Referring to FIG. 6, circumferential notch 39 of barrel 30 fits into waist 55 of sealing member 50 to prevent sealing member 50 being drawn back into barrel 30.

As evident in FIG. 6, teeth 47A-L of serrated rim 46 of needle mount body 42 interact with guiding clips 35A-F in barrel 30 to facilitate positioning of needle mount 40 at needle end 32 of barrel 30. Each guiding clip 35 has a guiding tooth 37 which, during assembly, assists fitting of needle mount 40 into needle end 32 of barrel 30 by engaging adjacent teeth 47. In the example shown in FIGS. 5 and 6, teeth 47A,B interact with tooth 37A of guiding clip 35A, and teeth 47E,F interact with tooth 37C of guiding clip 35C, although it will be appreciated that any pair of adjacent teeth 47 may interact with any guiding clip 35.

This arrangement also prevents rotation of needle mount 40 when a complementary screw-threaded needle is mounted to luer mount 41 via locking thread 43.

Needle end 32 of barrel 30 also comprises holding clips 36A-F which engage underside 48 of serrated rim 46 of needle mount 40 and prevent inadvertent withdrawal of needle mount 40 into barrel 30 prior to retraction. Holding clips 36A, D are shown in FIG. 6. Holding clips 36A-D are suitable formed of a material that is resiliently deformable so that holding clips 36A-D can be released from engagement with needle mount 40 but are not so deformable that they inadvertently disengage needle mount 40 during withdrawal of plunger 20 prior to retraction.

Figure 7:
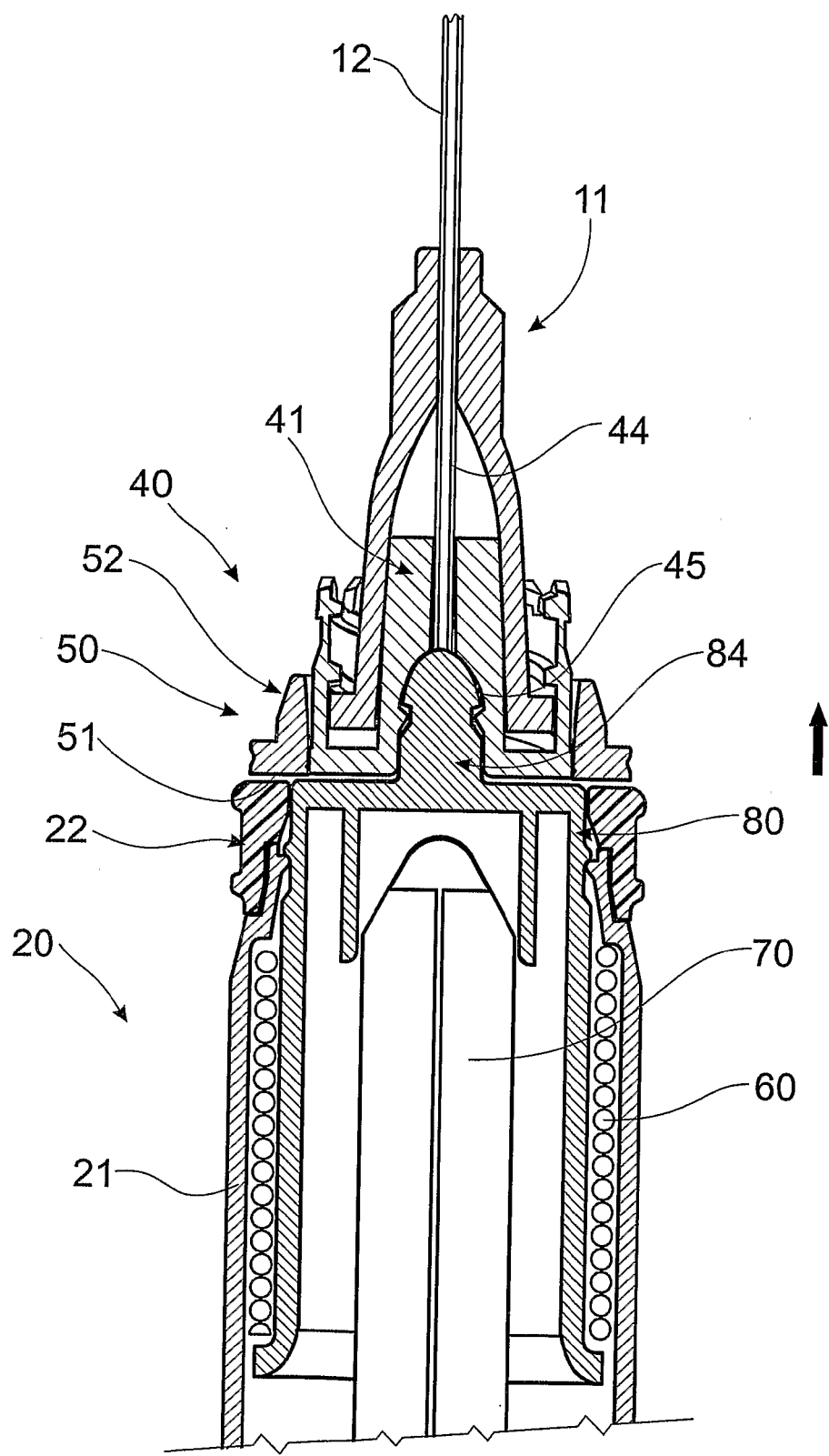
FIG. 7 is a sectional view of a plunger engaging a needle mount prior to retraction.
Figure 8:
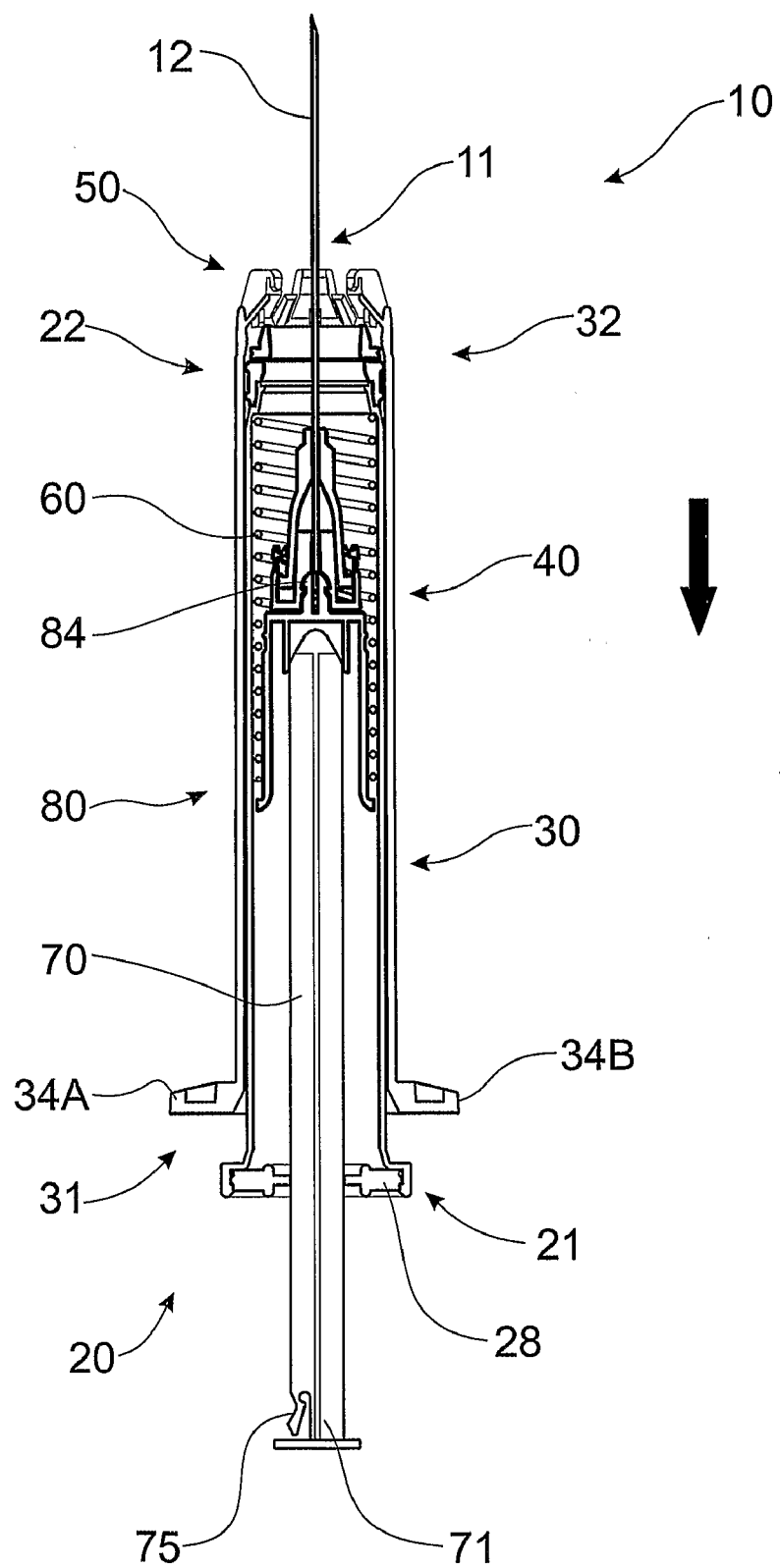
FIG. 8 is a side sectional view of a retractable syringe during retraction of needle mount, plunger member and plunger rod.

Referring now to FIG. 7 and FIG. 8, the sequence of events that occur in use is as follows.

Syringe 10 is typically, although not exclusively, capable of delivering a 3 or 5 mL fluid volume. So that plunger member 80 does not accidentally engage needle mount 40 prior to retraction, barrel 30 is of sufficient capacity to allow withdrawal of plunger 20 to fill barrel 30 with fluid from an initial position proximal to needle mount 40 (i.e towards plunger end 31 of barrel 30).

Once filled, injection of fluid contents of barrel 30 is achieved by depression of plunger 20.

Toward the end of depression of plunger 20 to deliver fluid from fluid space 500, needle mount engaging means 84 of plunger member 80 snap-lock engages complementary mating recess 45 of needle mount 40 to thereby couple needle mount 40 and plunger member 80. This is achieved by male members 85A, 85B, 85C of needle mount engaging means 84 being capable of radial inward movement into gaps 87A, 87B, 87C (as shown by the solid arrows in FIG. 4) to facilitate entry into, and engagement with, complementary mating recess 45, as shown in FIG. 7.

With continued depression of the plunger 20 in the direction of the solid arrow in FIG. 7, tapered ejector means 52 of sealing member 50 is pushed toward needle end 32 of barrel 30 by plunger seal 22 coupled to plunger housing 21 bearing against sealing base 51. Plunger seal 22 and plunger housing 21 continue to move in this direction while plunger member 80 couples with needle mount 40 and momentarily stops moving.

This continued movement of sealing member 50 with tapered ejector means 52 toward needle end 32 of barrel 30 allows ejector means 52 to move holding clips 36A-F radially outwardly (as shown by solid arrows in FIG. 6) and out of engagement with underside 48 of serrated rim 46 of needle mount 40, thereby releasing needle mount 40, which is coupled to plunger member 80 as hereinbefore described, from needle end 32 of barrel 30.

With slight continued depression of plunger 20, plunger member 80 is released from engagement with plunger housing 21. This is achieved by outer circumferential ledge 81A of plunger member 80 uncoupling from inner circumferential shoulder 25A in neck 24 of plunger housing 21 to release engagement between plunger housing 21 and plunger member 80.

This disengagement allows decompression of spring 60 to push against outer circumferential ledge 81B of plunger member 80 to thereby retract plunger member 80 and needle mount 40 coupled therewith inside plunger housing 21 in the direction of the arrow in FIG. 8, while leaving sealing member 50 and plunger seal 22 stationary. Likewise, under spring 60 pressure control rod 70 disengages from plug member 28 fitted into plunger housing 21 by way of spring clip 75 moving out of engagement with inner circumferential shoulder 29 of plug member in the direction indicated by the arrow in FIG. 3. Thus, plunger rod 70 retracts, the rate of which retraction is controlled by a user exerting pressure (such as by way of thumb pressure) against control button 71.

Retraction is complete when ledge 81B of plunger member 80 abuts plug member 28.

Plunger housing 21, plunger seal 22 and sealing member 50 do not retract and remain at needle end 32 of barrel 30.

Figure 9:
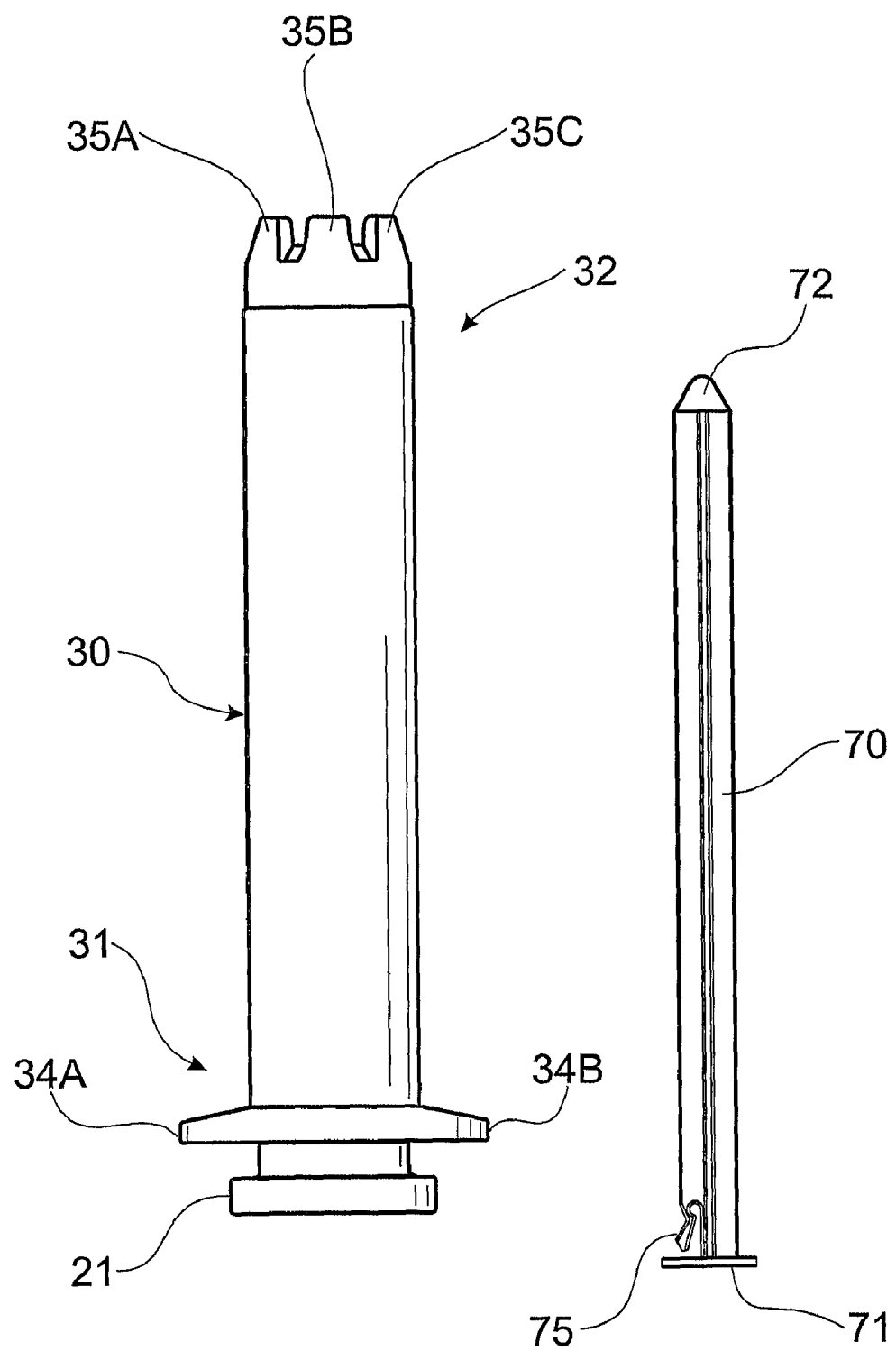
FIG. 9 is a side view of a retractable syringe with a disengaged control rod after retraction.
Figure 10:
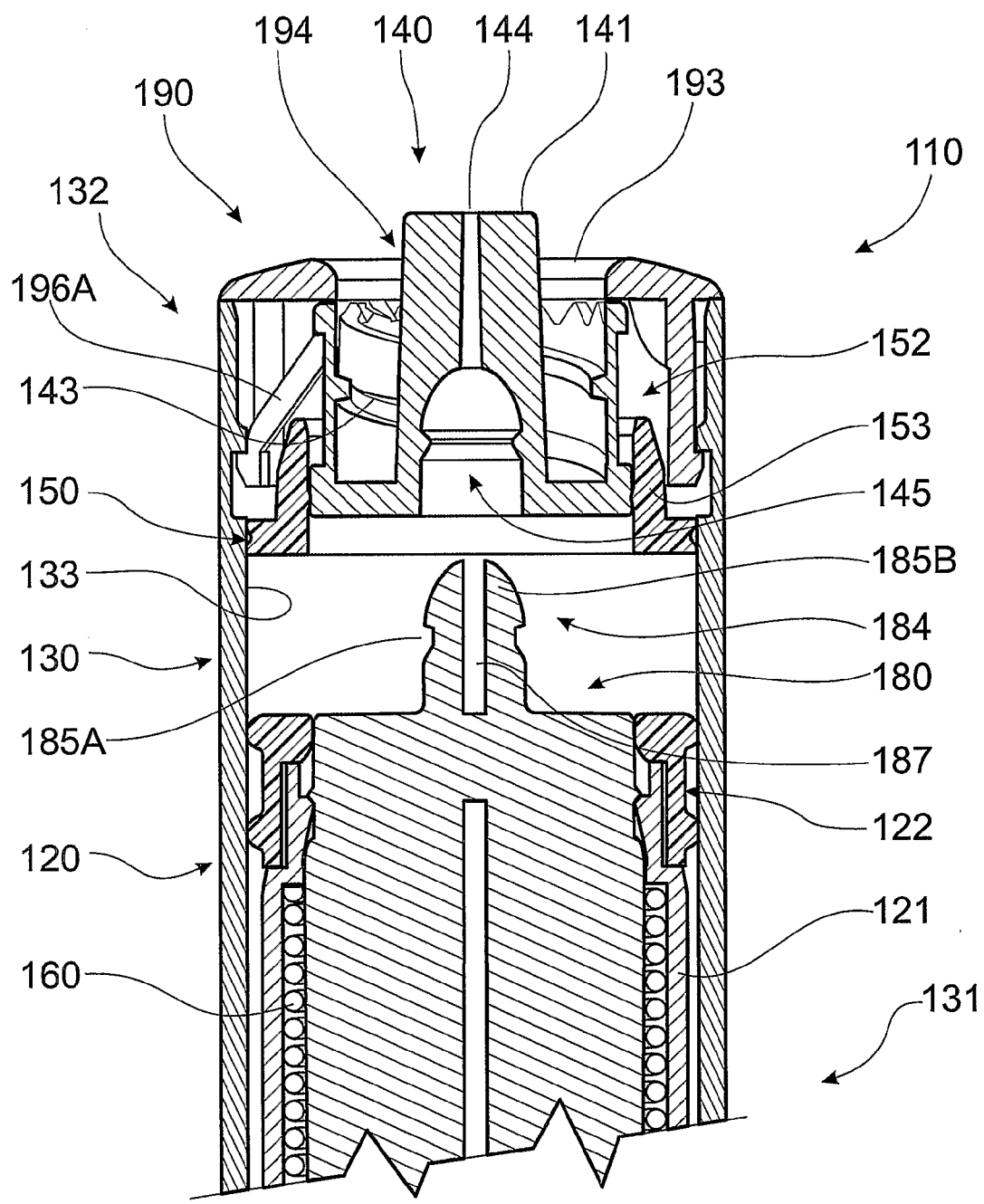
FIG. 10 is a sectional view of an embodiment of a retractable syringe showing a cap mounted to a barrel.

As shown in FIG. 9, control rod 70 can then be manually removed from syringe 10. Control rod 70 may be discarded as "clean" waste, leaving syringe 20 with plunger housing 21, plunger seal 22 and sealing member 50 remaining inside barrel 30 for a more compact medical waste disposal.

An alternative embodiment is shown in FIGS. 10-13, wherein retractable syringe 110 comprises plunger 120 and barrel 130. Barrel 130 comprises plunger end 131, needle end 132, inside wall 133 and finger grips 134A, 134B at plunger end 131. At needle end 131 of barrel 130 is mounted retractable needle mount 140 with needle 111 comprising cannula 112, cap 190 and sealing member 150.

Plunger member 180 comprises needle mount engaging means 184 comprising male members 185A, 185B separated by gap or space 187, which is capable of engaging mating recess 145 of needle mount 140.

Figure 11:
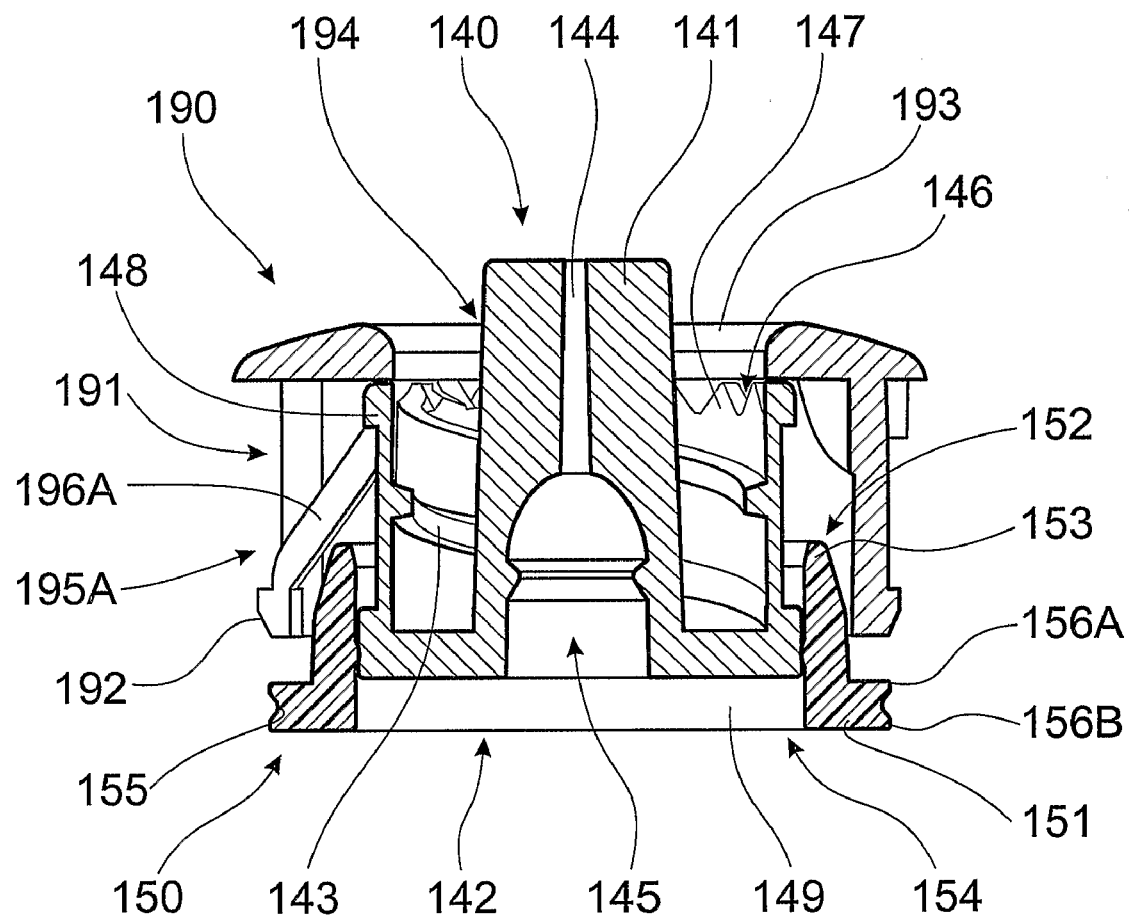
FIG. 11 is a side sectional view of an embodiment of a barrel cap, needle mount and sealing member.

Referring to FIG. 11, cap 190, retractable needle mount 140 and sealing member 150 are described in more detail.

Cap 190 comprises cap body 191, base rim 192, cover 193 and luer aperture 194. Body 191 comprises spaces 195A, 195B, 195C associated with respective holding clips 196A, 196B, 196C. Holding clips 196B, 196C and corresponding spaces 195B, 195C are not visible in FIG. 11, but can be seen more clearly in FIG. 12 and FIG. 13.

Referring again to FIG. 11, needle mount 140 comprises body 142 having luer mount 141 with locking thread 143 and central bore 144 which allows fluid communication between a needle (not shown) mounted to luer mount 141 and fluid contents of barrel 130. In an alternative embodiment, luer mount 141 may be in the form of a non-threaded luer slip (not shown) as is well known in the art.

Central bore 144 communicates with mating recess 145 that receives needle mount-engaging means 184 of plunger 120 to facilitate retraction of needle mount 140 and a needle engaged therewith, as previously described.

Needle mount body 142 further comprises serrated rim 146, which comprises a plurality of teeth 147 and rim underside 148, and needle mount base 149.

Sealing member 150 comprises sealing base 151 and ejector means 152 in the form of tapered annulus 153, together with needle mount aperture 154.

Sealing member 150 is fitted around needle mount base 149 and partly within cap 190 which is mounted over needle mount body 142 so that luer mount 141 projects through luer aperture 194 of cap 190.

According to this embodiment, holding means is provided that comprises holding clips 196A, 196B, 196C of cap 190, inwardly oriented so as to abut against underside 148 of serrated rim 146 to prevent movement of needle mount 140 toward plunger end 131 of barrel 130 during withdrawal of plunger during filling of syringe 110. Holding clips 196A, 196B, 196C of cap 190 are capable of radially outward deformation as indicated by the solid arrows in FIG. 13, to allow release of needle mount 140.

Figure 12:
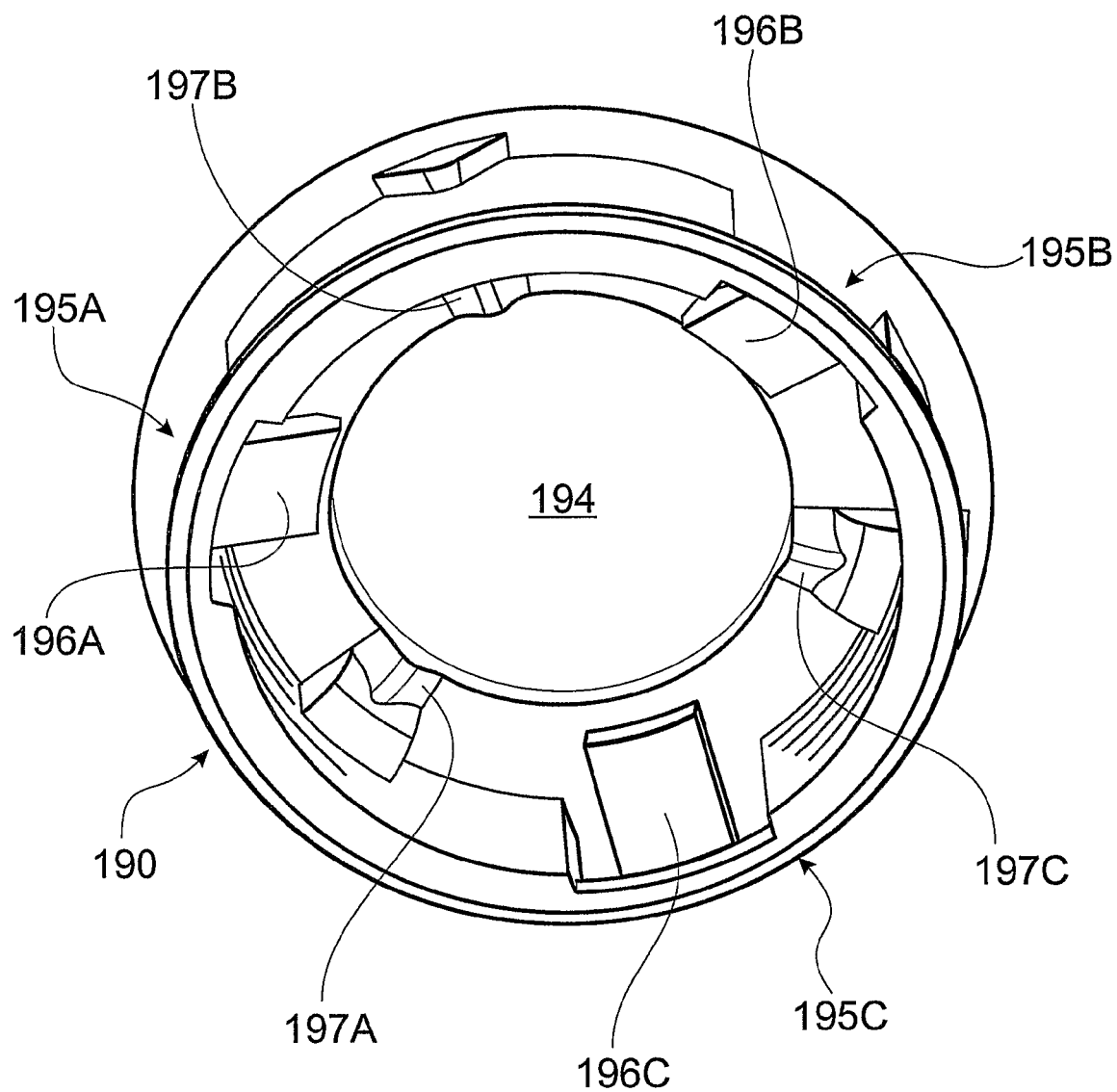
FIG. 12 is a top sectional view of an embodiment of a barrel cap.
Figure 13:
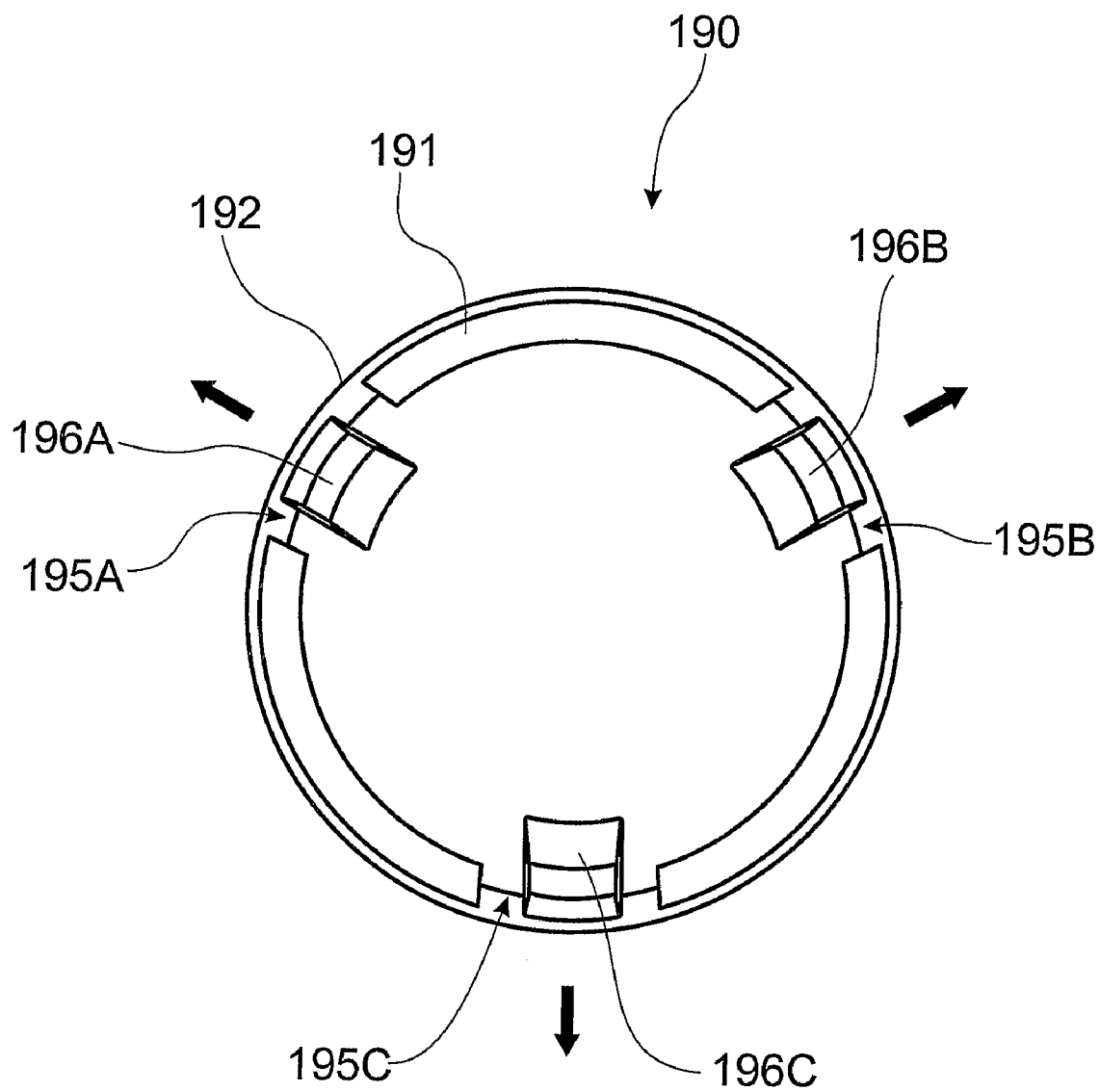
FIG. 13 an end view inside a cap.

Teeth 147 of serrated rim 146 of needle mount body 141 interact with complementary teeth 197A, 197B, 197C in underside of cap 190 as shown in FIG. 12, to thereby prevent rotation of needle mount 140 when a complementary screw-threaded needle is mounted to luer mount 141 via locking thread 143.

As previously described, following engagement of needle mount 140 by plunger member 180, continued depression of plunger 120 pushes tapered ejector means 152 of sealing member 150 toward needle end 132 of barrel 130 to allow ejector means 152 to urge holding clips 196A, 196B, 196C radially outwardly (as shown by solid arrows in FIG. 13) and out of engagement with underside 148 of serrated rim 146 of needle mount 140, thereby releasing needle mount 140 which is coupled to plunger member 180 as hereinbefore described.

Spring 160 decompression and controlled retraction of needle mount 140 and needle 111 mounted thereto are essentially as hereinbefore described.

The foregoing preferred embodiments relate typically, although not exclusively, to a retractable syringe 10 wherein a needle 11 may be mounted to a needle mount 40 by way of a luer slip or luer lock.

An alternative embodiment having a fixed cannula 211 is shown in FIGS. 14-17.

Figure 14:
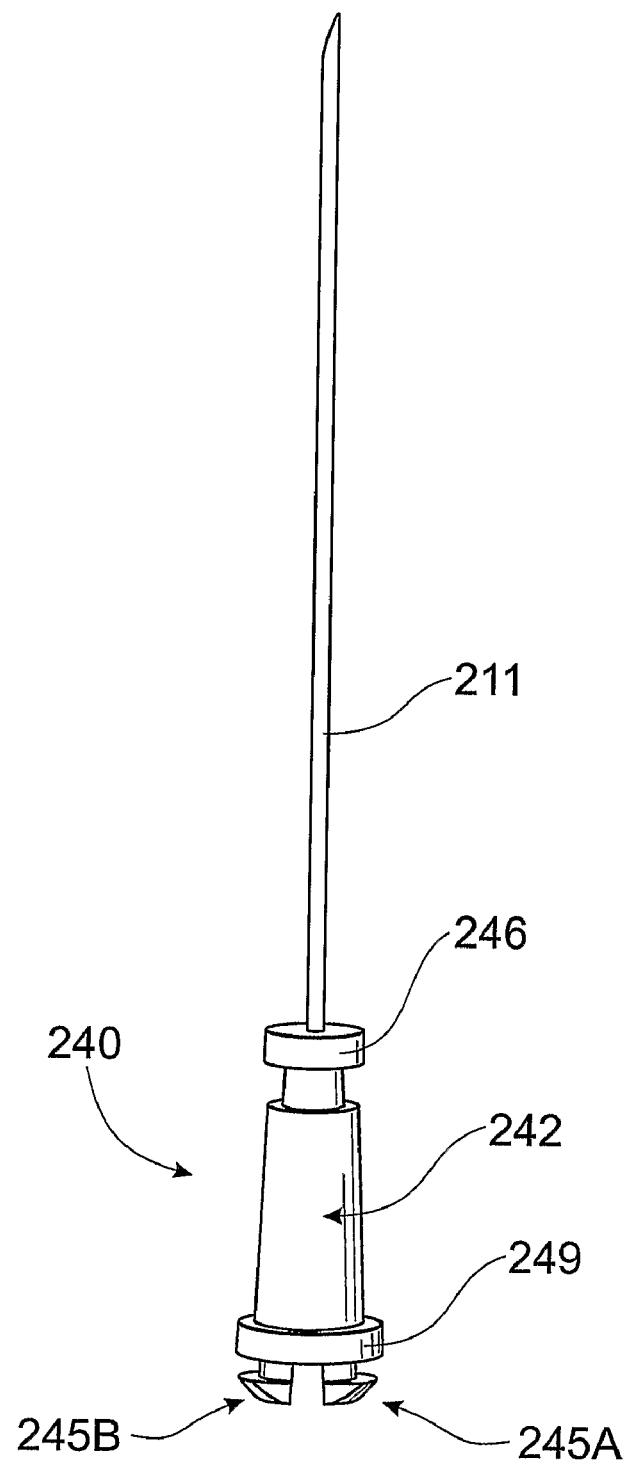
FIG. 14 is a perspective view of an alternative embodiment of a needle and needle mount.

According to this embodiment and particularly referring to FIG. 14, cannula 211 is glued or co-moulded into needle mount 240 Needle mount 240 comprises body 242 having rim 246, base 249 and plunger-engaging means in the form of barbs 245A, 245B.

Figure 15:
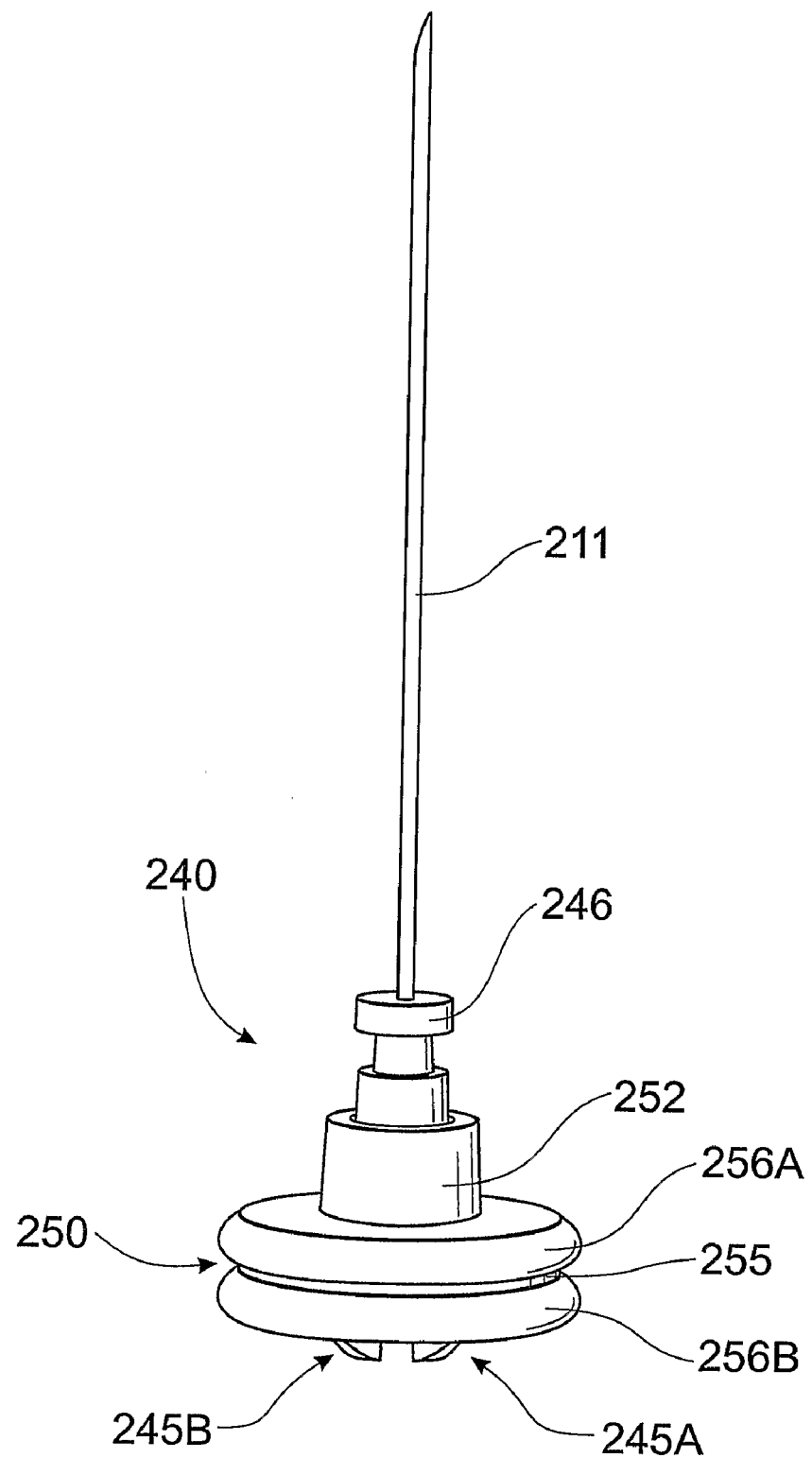
FIG. 15 is a perspective view of an alternative embodiment of a needle, needle mount and sealing member.

Referring now to FIG. 15, ejector means 252 is co-moulded onto sealing member 250. Sealing member 250 acts to seal inside wall 233 of barrel 230 by way of sealing ribs 256A, 256B separated by waist 255 and needle mount 240 on base 249. An advantage of this arrangement is that the fixed needle 211 is typically of smaller diameter than a luer slip or luer lock needle mount 240, hence reducing the overall diameter of syringe 210.

Figure 16:
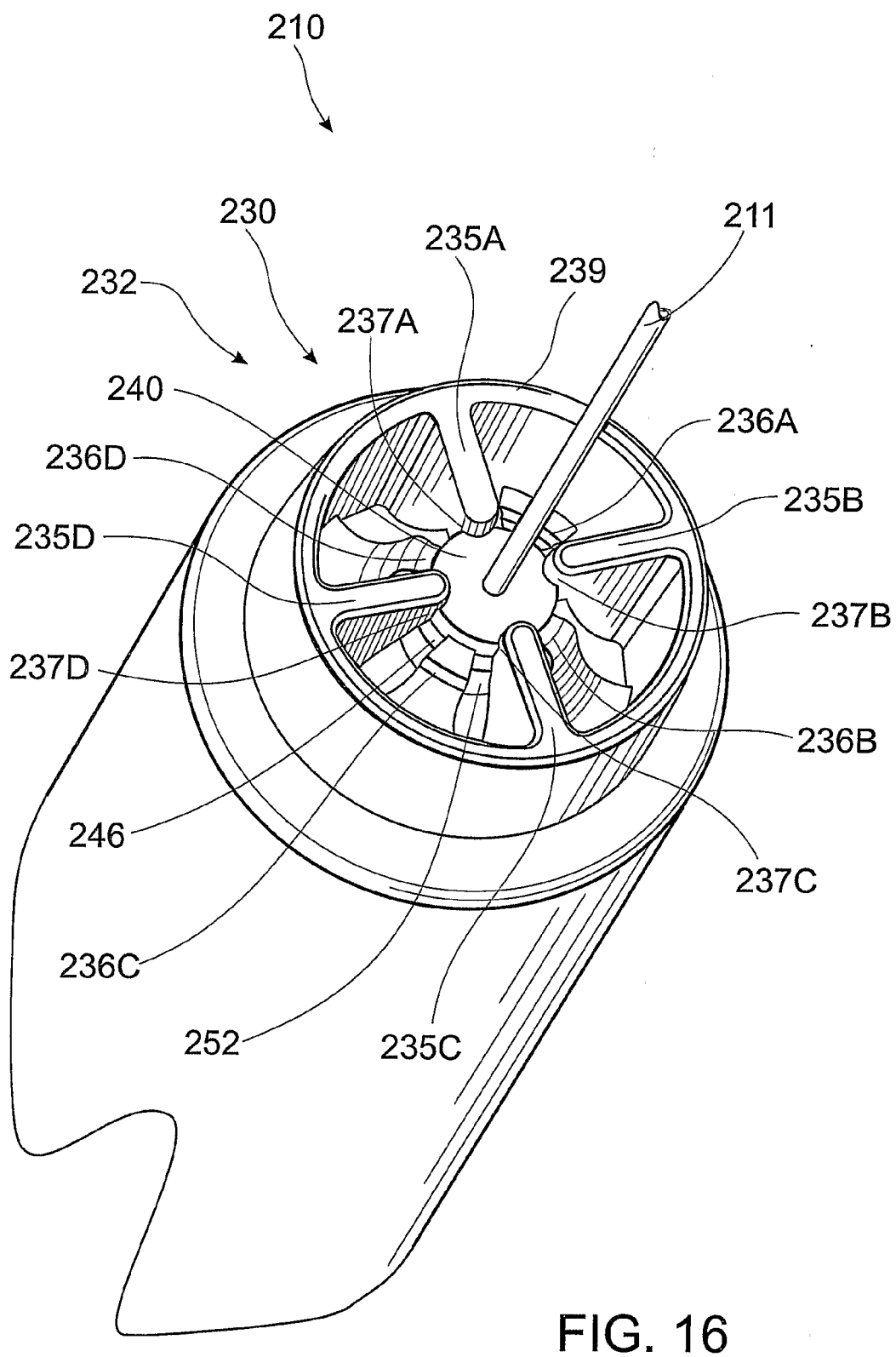
FIG. 16 is a perspective view of an alternative embodiment of a barrel comprising an integrally formed holding means.

Referring now to FIG. 16, at needle end 232 of barrel 230, holding means comprises plurality of holding clips moulded in collar 239 of barrel 230. Holding clips 236A, 236B, 236C, 236D engage needle mount 240 to prevent inadvertent retraction of needle 240 during withdrawal of plunger 220 to fill syringe 210 with fluid. Guiding clips 235A, 235B, 235C, 235D are integrally formed in barrel collar 239 of barrel 230 and each guiding clip 235 has a ledge 237 which, during assembly, assists fitting of needle mount 240 into needle end 232 of barrel 230 and prevents movement of needle mount body beyond needle end 232 by engaging rim 246 of needle mount 240.

Figure 17:
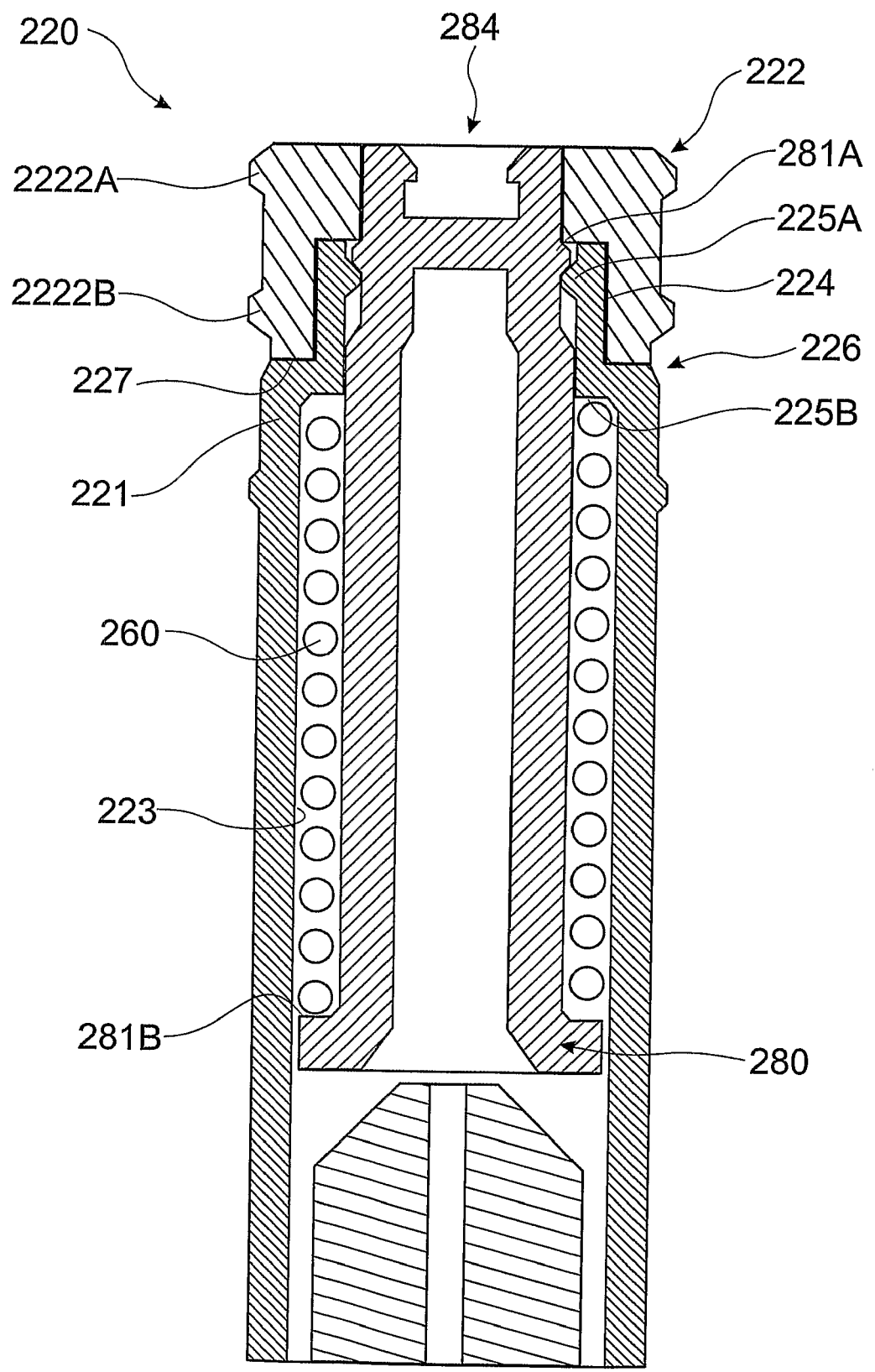
FIG. 17 is a sectional view of an alternative embodiment of a plunger.

According to this embodiment, and referring particularly to FIG. 17 plunger 220 comprises plunger housing 221, plunger member 280 and plunger seal 222. Plunger seal 222 is co-moulded onto plunger housing 221 and comprises sealing ribs 2222A, 2222B.

Needle mount engaging means 284 is a recess in plunger member 280 adapted to receive barbs 245A, 245B of needle mount 240 to facilitate retraction of needle mount 240 as hereinbefore described.

Seat 227 of plunger seal 222 seals onto neck 224 of plunger housing 221 and bears against plunger member 280 at junction 226, whilst also providing a fluid seal between plunger sealing members 2222A, 2222B and barrel 230.

Compressed spring 260 is mounted to plunger member 280, held between outer circumferential ledge 281B of plunger member 280 and inner circumferential shoulder 225B of inner wall 223 of plunger housing 221. Outer circumferential ledge 281A of plunger member 280 bears against inner circumferential shoulder 225A of plunger housing 221 to thereby maintain releasable engagement between plunger housing 221 and plunger member 280.

However, in particular embodiments, circumferential ledge 281A of plunger member 280 and/or inner ledge 225A of plunger housing 221 may be segmented, for example comprising two, three, four, five or six annular segments. Preferably, each segment may be of equal length.

It is anticipated that this segmented arrangement may provide a tighter interference fit so that even with tolerance variation that often occurs with injection moulding, coupling will be strong enough to maintain compression of spring 260, but require less force to uncouple plunger member 280 from plunger 221 and thereby allow spring 260 to decompress and facilitate retraction of needle mount 240 and cannula 21.

In light of the foregoing it will be appreciated that the present invention provides a relatively simple, robust and inexpensive retractable syringe that is automatically disabled with little or no assistance from the user to thereby prevent, or at least minimize the likelihood of, re-use of the syringe.

Furthermore, by controlling the rate of needle retraction, the likelihood of blood splattering is reduced thereby improving the "user-friendliness" of the retractable syringe.

A particular advantage of the retractable syringe of the invention is that the plunger does not need to be rotated into alignment with the needle mount in order to allow retraction of the needle mount.

Furthermore, the ejector means is symmetrical, thereby obviating the need for alignment with the holding clips to effect release of the needle mount.

Accordingly, this non-requirement for orientation greatly simplifies manufacture and thereby reduces the manufacture cost and sale price of the syringe.

Throughout the specification, the aim has been to describe the preferred embodiments of the invention without limiting the invention to any one embodiment or specific collection of features. Various changes and modifications may be made to the embodiments described and illustrated without departing from the present invention.

The invention claimed is:

1. A plunger for a retractable syringe having a barrel and a retractable needle mount to which is mounted or is mountable to a needle, said plunger comprising: a plunger member including an engagement apparatus configured to engage with the retractable needle mount; a plunger housing; a spring positioned inside the plunger housing, but outside the plunger member such that the plunger housing and the plunger member cooperate to maintain the spring in an initially compressed state prior to a retraction of the retractable needle mount; and a retractable removable control device configured to facilitate control of a rate of retraction of the retractable needle mount when engaged with the plunger member and the needle is being retracted, wherein the removable control device has a first end configured with a nub to engage a ring of the plunger member, and a second end configured to allow manual control over the rate of retraction of the retractable needle mount.

2. The plunger of claim 1, further comprising a plunger seal integrally formed with the plunger housing.

3. The plunger of claim 2, wherein the plunger seal is insert moulded into the plunger housing.

4. The plunger of claim 1, arranged so that decompression of the spring facilitates disengagement of the ring and nub to thereby allow release of the removable control device from the plunger housing.

5. The plunger of claim 4, wherein the control device is a control rod.

6. The plunger of claim 1, arranged so that release of the plunger member from the plunger housing allows decompression of the spring to facilitate retraction of the retractable needle when the plunger member is engaged to the needle mount.

7. A syringe having a barrel; a retractable needle mount to which is mounted or is mountable to a needle; and a plunger comprising: a plunger member including an engagement apparatus configured to engage with the retractable needle mount; a plunger housing; a spring positioned inside the plunger housing, but outside the plunger member such that the plunger housing and the plunger member cooperate to maintain the spring in an initially compressed state prior to retraction of the retractable needle mount; and a retractable removable control device configured to facilitate control of a rate of retraction of the retractable needle mount when engaged with the plunger member and the needle is being retracted, wherein the removable control device has a first end configured with a nub to engage a ring of the plunger member, and a second end configured to allow manual control over the rate of retraction of the retractable needle mount.

8. The retractable syringe of claim 7, further comprising a holding apparatus configured to releasably engage the needle mount to thereby prevent retraction of the retractable needle mount during withdrawal of the plunger.

9. The syringe of claim 8, wherein the syringe further comprises an ejector device configured operable to release the holding apparatus from engagement with the needle mount to thereby allow retraction of the retractable needle mount.

10. The syringe of claim 9, arranged so that release of the plunger member from the housing allows decompression of the spring to facilitate the retraction of the retractable needle mount when said the plunger member is engaged to the retractable needle mount.

11. The syringe of claim 8, further comprising a sealing member fitted to the needle mount, wherein the sealing member remains at a needle end of the barrel following the retraction of the retractable needle mount.

12. The syringe of claim 11, wherein the sealing member comprises an ejector device operable to release the holding apparatus from engagement with the needle mount to thereby allow the retraction of the retractable needle mount.

13. The syringe of claim 8, wherein the holding means comprises holding clips integrally formed in the barrel.

14. The syringe of claim 8, wherein the holding apparatus comprises holding clips in a cap mounted to the barrel.

15. The retractable syringe of claim 7, further comprising a plunger seal integrally formed with the plunger housing.

16. The retractable syringe of claim 15, wherein the plunger seal is insert moulded into the plunger housing.

17. The syringe of claim 7, arranged so that decompression of the spring facilitates disengagement of the nub and the ring to thereby allow release of the control device from the plunger housing.

18. A syringe comprising a barrel, a retractable needle mount to which is mounted or is mountable to a needle; a plunger comprising a plunger housing, a plunger member and a spring positioned inside the plunger housing, but outside the plunger member, the plunger housing and the plunger member co-operating to maintain the spring in an initially compressed state prior to retraction of the retractable needle mount; a holding device configured to releasably engage the needle mount to thereby prevent retraction of the retractable needle mount during withdrawal of the plunger; and a sealing member comprising ejector device operable to release the holding device from engagement with the needle mount to thereby allow retraction of the needle mount; the plunger member comprising an engagement apparatus configured to engage the retractable needle mount, an integrally formed plunger seal and a retractable removable control device configured to facilitate control of a rate of retraction of the retractable needle mount when engaged with the plunger and the needle is being retracted, the plunger is configured to releasably couple the controlling apparatus to the plunger housing prior to retraction of the retractable needle mount, wherein the removable control device has a first end configured with a nub to engage a ring of the plunger member, and a second end configured to allow manual control over the rate of retraction of the retractable needle mount.

19. The syringe of claim 18, arranged so that decompression of said spring facilitates disengagement of the nub and the ring to thereby allow release of the control device from the plunger housing.

20. A plunger for a syringe having a barrel and a retractable needle mount to which is mounted or is mountable to a needle, the plunger comprising a plunger housing, a plunger member and a spring positioned inside the plunger housing, but outside the plunger member, the plunger housing and the plunger member co-operating to maintain the spring in an initially compressed state prior to a retraction of the retractable needle mount, the plunger member comprising an engagement apparatus configure to engage with the retractable needle mount, an integrally formed plunger seal and a retractable removable control device configured to facilitate control of a rate of retraction of the retractable needle mount when engaged with the plunger member and the needle is being retracted, the plunger further comprising a ring configured to releasably couple a nub of a first end of the removable control device to the plunger housing prior to retraction of the retractable needle mount, and a second end configured to allow manual control over the rate of retraction of the retractable needle mount.

* * * * *